(12) United States Patent
Mundy et al.

(10) Patent No.: US 7,058,210 B2
(45) Date of Patent: Jun. 6, 2006

(54) METHOD AND SYSTEM FOR LUNG DISEASE DETECTION

(75) Inventors: Joseph Leagrand Mundy, Schenectady, NY (US); Colin Craig McCulloch, Charlton, NY (US); Ricardo Scott Avila, Clifton Park, NY (US); Shannon Lee Hastings, Clifton Park, NY (US); Robert August Kaucic, Jr., Niskayuna, NY (US); William Edward Lorensen, Ballston Lake, NY (US); Matthew William Turek, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 615 days.

(21) Appl. No.: 09/683,111

(22) Filed: Nov. 20, 2001

(65) Prior Publication Data

US 2003/0095692 A1 May 22, 2003

(51) Int. Cl.
*G06K 9/00* (2006.01)
(52) U.S. Cl. .................................. 382/128
(58) Field of Classification Search .............. 382/128
See application file for complete search history.

(56) References Cited

U.S. PATENT DOCUMENTS

| | | | |
|---|---|---|---|
| 4,710,876 A | 12/1987 | Cline et al. | 364/414 |
| 4,751,643 A | 6/1988 | Lorensen et al. | 364/414 |
| 4,907,156 A | 3/1990 | Doi et al. | 364/413.13 |
| 5,235,510 A | 8/1993 | Yamada et al. | 364/413.02 |
| 5,331,550 A | 7/1994 | Stafford et al. | 364/413.02 |
| 5,359,513 A | 10/1994 | Kano et al. | 364/413.23 |
| 5,437,279 A * | 8/1995 | Gray | 600/427 |
| 5,692,507 A | 12/1997 | Seppi et al. | 128/653.1 |
| 5,779,634 A | 7/1998 | Ema et al. | 600/407 |
| 5,832,103 A | 11/1998 | Giger et al. | 382/130 |
| 5,881,124 A | 3/1999 | Giger et al. | 378/8 |
| 5,943,435 A | 8/1999 | Gaborski | 382/132 |
| 5,987,094 A | 11/1999 | Clarke et al. | 378/62 |

(Continued)

OTHER PUBLICATIONS

Matthew S. Brown et al., "Method For Segmenting Chest CT Image Data Using An Anatomical Model: Preliminary Results", IEEE Transactions on Medical Imaging, IEEE Inc, New York, U.S., vol. 16. No. 6. Dec. 1997, pp. 828-839.*

(Continued)

*Primary Examiner*—Brian Werner
*Assistant Examiner*—Christopher Lavin
(74) *Attorney, Agent, or Firm*—Jean K. Testa; Patrick K. Patnode (57) ABSTRACT

A method for processing medical images for use in the detection and diagnosis of disease comprises classifying regions of interest within the medical images based on a hierarchy of anatomical models and signal models of signal information of an image acquisition device used to acquire the medical images. The anatomical models are derived to be representative of anatomical information indicative of a given disease. A computer-aided system for use in the diagnosis and detection of disease comprises an image acquisition device for acquiring a plurality of image data sets and a processor adapted to process the image data sets. The processor is adapted to classify selected tissue types within the image data sets based on a hierarchy of signal and anatomical models and the processor is further adapted to differentiate anatomical context of the classified tissue types for use in the diagnosis and detection of disease.

17 Claims, 4 Drawing Sheets

U.S. PATENT DOCUMENTS

| | | | | |
|---|---|---|---|---|
| 5,987,345 A | | 11/1999 | Engelmann et al. | 600/407 |
| 6,004,267 A | * | 12/1999 | Tewari et al. | 600/300 |
| 6,125,194 A | | 9/2000 | Yeh et al. | 382/132 |
| 6,272,470 B1 | * | 8/2001 | Teshima | 705/3 |
| 6,574,304 B1 | | 6/2003 | Hsieh et al. | 378/4 |

OTHER PUBLICATIONS

Tatsuya Kawahara et al., "HMM based on Pair-Wise Bayes Classifiers", Acoustics, Speech, and Signal Processing, 1992. ICASSP-92., 1992 IEEE International Conference on vol. 1, Mar. 23-26, 1992 pp.:365-368 vol. 1.*

Lee, Youngbum, Takeshi Hara, Hisroshi Fujita, Shigeki Itoh and Takeo Ishigaki, "Automated Detection Of Pulmonary Nodules In Helical CT Images Based On An Improved Template-Matching Technique", IEEE Transactions on Medical Imaging, vol. 20, No. 7, Jul. 2001, pp. 595-604.

John Canny, "A Computational Approach To Edge Detection", IEEE Transactions On Pattern Analysis and Machine Intelligence, vol. PAMI-8, No. 6, Nov. 1986, pp. 679-697.

Knapman, John and Will Dickson, "Hierarchical Probabilistic Image Segmentation", Image and Vision Computing, Sep. 1994, UK, vol. 12, No. 7, pp. 447-457.

Elliott, P.J and J.M. Knapman and W. Schegel, "Interactive Image Segmentation For Radiation Treatment Planning", IBM Systems Journal, IBM Corp. Armonk, New York, U.S., vol. 31, No. 4, 1992, pp. 620-634.

Matthew S. Brown et al., "Method For Segmenting Chest CT Image Data Using An Antomical Model: Preliminary Results", IEEE Trans on Med Imaging, IEEE Inc, New York, U.S., vol. 16, No. 6, Dec. 1, 1997, pp. 828-839.

Atam P Dhawan et al., "Knowledge-based Analysis and Recognition of 3D Images of Human Chest-Cavity", Visualization In Biomedical Computing, 1990, Proceedings of the First Conference on Atlanta, GA. USA May 22-25, 1990, pp. 162-169.

* cited by examiner

METHOD AND SYSTEM FOR LUNG DISEASE DETECTION

BACKGROUND OF INVENTION

This invention relates to a method and system for processing medical image data to aid in the detection and diagnosis of disease, and more particularly, to a method and system for detecting lung disease in medical images obtained from a x-ray computed tomography (CT) system.

A x-ray chest radiograph system is the more commonly used diagnostic tool useful for the purpose of detecting lung disease in humans. Lung disease such as bronchitis, emphesema and lung cancer are also detectable in chest radiographs and CT. However, CT systems generally provide over 80 separate images for a single CT scan thereby providing a considerable amount of information to a radiologist for use in interpreting the images and detecting suspect regions that may indicate disease.

Suspect regions are defined as those regions a trained radiologist would recommend following through subsequent diagnostic imaging, biopsy, functional lung testing, or other methods. The considerable volume of data presented by a single CT scan presents a time-consuming process for radiologists. Conventional lung cancer screening generally involves a manual interpretation of the 80 or more images by the radiologist. Fatigue is therefore a significant factor affecting sensitivity and specificity of the human reading. In other diseases, such as emphysema, it is difficult for a radiologist to classify the extent of disease progression by only looking at the CT images. Quantitative analysis of the anatomy is required.

Attempts to automate lung cancer and emphysema detection in CT scans have been based on a variety of nodule detection and classification techniques, and lung parenchyma metrics. The emerging field is referred to as Computer Aided Diagnosis, or alternatively, Computer Aided Detection (CAD). There is a significant amount of literature on methods for automating lung cancer detection in CT scans. Generally nodule detection has proceeded in three steps: lung segmentation, vessel extraction, and final nodule candidate detection and classification.

Vessel extraction has been attempted using gray-level thresholding, fuzzy clustering, and three-dimensional seeded region growing). Nodule detection has been done using template matching, genetic algorithms, gray-level thresholding, the N-Quoit filter, region growing, and edge-gradient techniques.

Once candidate nodules are produced by any of the above methods, classification has been implemented via rule-based methods, neural network classification, fuzzy logic, and statistical techniques including factor analysis and linear discriminating analysis.

The above techniques presented to date, however, have largely focused on identifying suspicious lesions in CT scans and have not directly addressed obtaining correct differentiation of structures in the lung and correct measurements of their size. Additionally, the above techniques are generally limited in the interpretative nature of the results. Typically, identification and classification of a lesion using the above techniques may produce a positive affirmation of a nodule, but further radiologist qualitative review and interpretation of results is generally required. For example, radiologists rely heavily on their familiarity with or expert knowledge of pathological and anatomical characteristics of various abnormal and normal structures in interpreting medical images. Further, the characteristics of the scanning device, such as type, pixel intensity and signal impulse response, also influence the presentation of the image data. A radiologist's interpretation of medical images also generally relies on his or her familiarity with a given scanner. There has been no apparent evaluation by the above techniques to address the type of or characteristics of the scanning device in the analysis of the images produced.

What is needed is a robust method and system for processing image data to produce quantitative data to be used in detecting disease. What is further needed is a method and system that provides interpretative results based on expert knowledge of a disease as well as the scanner capabilities and characteristics. Additionally, there is a requirement for the ability to track a disease's progression/regression resulting from drug therapy.

SUMMARY OF INVENTION

In a first aspect, a method for processing medical images for use in the detection and diagnosis of disease is provided. The method comprises classifying regions of interest within the medical images based on a hierarchy of anatomical models and signal models of signal information of an image acquisition device used to acquire the medical images. The anatomical models are derived to be representative of anatomical information indicative of a given disease.

In a second aspect, a computer-aided system for use in the diagnosis and detection of disease is provided. The system comprises an image acquisition device for acquiring a plurality of image data sets and a processor adapted to process the image data sets. The processor is adapted to classify selected tissue types within the image data sets based on a hierarchy of signal and anatomical models and the processor is further adapted to differentiate anatomical context of the classified tissue types for use in the diagnosis and detection of disease.

BRIEF DESCRIPTION OF DRAWINGS

The features and advantages of the present invention will become apparent from the following detailed description of the invention when read with the accompanying drawings in which.

DETAILED DESCRIPTION

Figure 1:
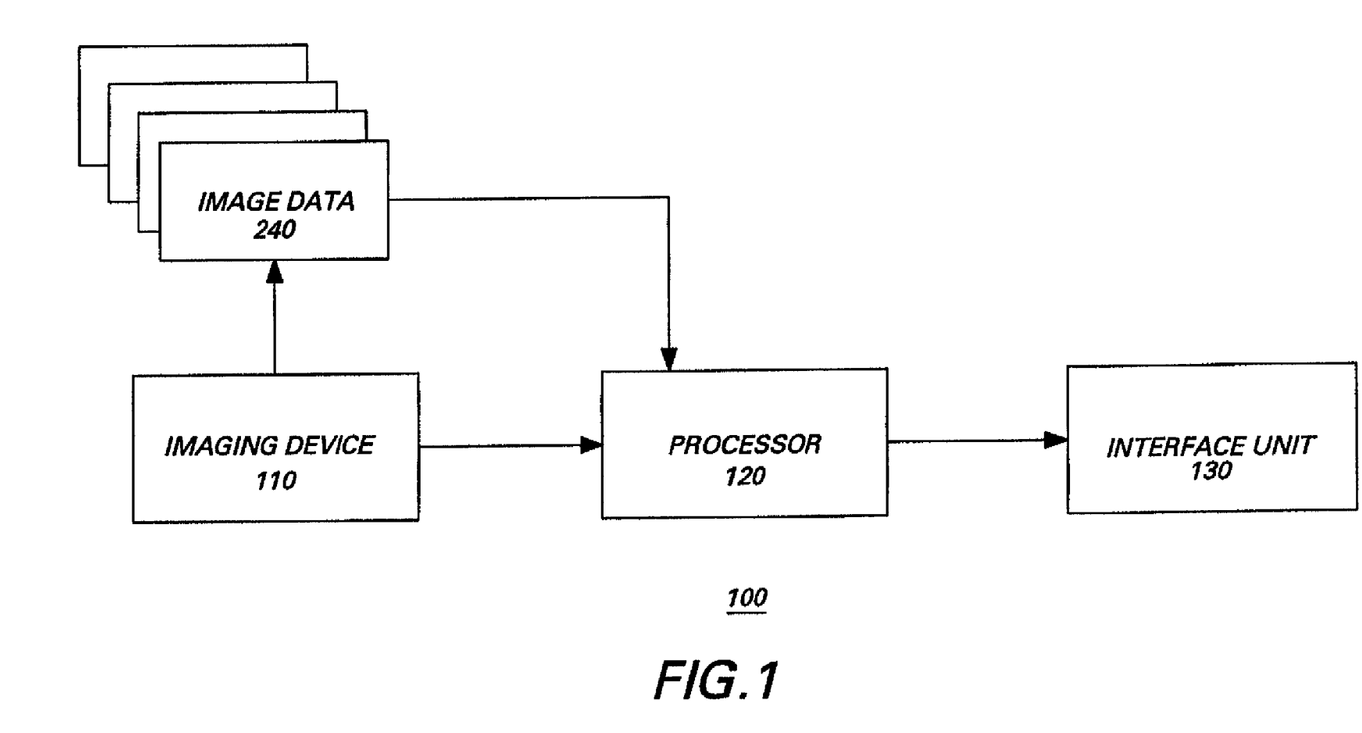
FIG. 1 is a block diagram illustration of a medical imaging system for which embodiments of the present invention are applicable.

Referring to FIG. 1, a general block diagram of a system 100 for disease detection is shown. System 100 includes an imaging device 110, which can be selected from a number of medical imaging devices known in the art for generating a plurality of images. Most commonly, computed tomography (CT) and magnetic resonance imaging (MRI) systems are used to generate a plurality of medical images.

During a CT imaging session, a patient lies horizontal and is exposed to a plurality of x-rays measured with a series of X-ray detectors. A beam of x-rays passes through a particular thin cross-section or "slice" of the patient. The detectors measure the amount of transmitted radiation. This information is used to compute the x-ray attenuation coefficient for sample points in the body. A gray scale image is then constructed based upon the calculated x-ray attenuation coefficients. The shades of gray in the image contrast the amount of x-ray absorption of every point within the slice. The slices obtained during a CT session can be reconstructed to provide an anatomically correct representation of the area of interest within the body that has been exposed to the x-rays.

During a MR imaging session, the patient is placed inside a strong magnetic field generated by a large magnet. Magnetized protons within the patient, such as hydrogen atoms, align with the magnetic field produced by the magnet. A particular slice of the patient is exposed to radio waves that create an oscillating magnetic field perpendicular to the main magnetic field. The slices can be taken in any plane chosen by the physician or technician (hereinafter the "operator") performing the imaging session. The protons in the patient's body first absorb the radio waves and then emit the waves by moving out of alignment with the field. As the protons return to their original state (before excitation), diagnostic images based upon the waves emitted by the patient's body are created. Like CT image slices, MR image slices can be reconstructed to provide an overall picture of the body area of interest. Parts of the body that produce a high signal are displayed as white in an MR image, while those with the lowest signals are displayed as black. Other body parts that have varying signal intensities between high and low are displayed as some shade of gray.

Once initial MR or CT images have been obtained, the images are generally segmented. The segmentation process classifies the pixels or voxels of an image into a certain number of classes that are homogeneous with respect to some characteristic (i.e. intensity, texture, etc.). For example, in a segmented image of the brain, the material of the brain can be categorized into three classes: gray matter, white matter, and cerebrospinal fluid. Individual colors can be used to mark regions of each class after the segmentation has been completed. Once the segmented image is developed, surgeons can use the segmented images to plan surgical techniques.

Generally, creating a segmented CT or MR image involves several steps. A data set is created by capturing CT or MR slices of data. Through the segmentation process, a gray scale value is then assigned to each point in the data set and different types of tissues will have different gray scale values. Each type of material in the data is assigned a specific value and, therefore, each occurrence of that material has the same gray scale value. For example, all occurrences of bone in a particular image may appear in a particular shade of light gray. This standard of coloring allows the individual viewing the image to easily understand the objects being represented in the images.

FIG. 1 illustrates a medical imaging system 100 to which embodiments of the invention are applicable. The system includes an imaging device 110, a processor 120 and an interface unit 130. Imaging device 110 is adapted to generate a plurality of image data sets 240 and is, for example, a computed tomography (CT) or magnetic resonance (MR) scanner. In the context of CT or MR, acquisition of image data is generally referred to as "scans". Processor 120 is configured to perform computations in accordance with embodiments of the present invention which will be described in greater detail with reference to FIGS. 2–4. Processor 120 is also configured to perform computation and control functions for well-known image processing techniques such as reconstruction, image data memory storage, segmentation and the like. Processor 120 may comprise a central processing unit (CPU) such as a single integrated circuit, such as a microprocessor, or may comprise any suitable number of integrated circuit devices and/or circuit boards working in cooperation to accomplish the functions of a central processing unit. Processor 120 desirably includes memory. Memory within processor 120 may comprise any type of memory known to those skilled in the art. This includes Dynamic Random Access Memory (DRAM), Static RAM (SRAM), flash memory, cache memory, etc. While not explicitly shown in FIG. 1, the memory may be a single type of memory component or may be composed of many different types of memory components. Processor 120 is also capable of executing the programs contained in memory and acting in response to those programs or other activities that may occur in the course of image acquisition and image viewing. As used herein, "adapted to", "configured" and the like refer to mechanical or structural connections between elements to allow the elements to cooperate to provide a described effect; these terms also refer to operation capabilities of electrical elements such as analog or digital computers or application specific devices (such as an application specific integrated circuit (ASIC)) that are programmed to perform a sequel to provide an output in response to given input signals.

Interface unit 130 is coupled to processor 120 and is adapted to allow human users to communicate with system 100. Processor 120 is further adapted to perform computations that are transmitted to interface unit 130 in a coherent manner such that a human user is capable of interpreting the transmitted information. Transmitted information may include images in 2D or 3D, color and gray scale images, and text messages regarding diagnosis and detection information. Interface unit 130 may be a personal computer, an image work station, a hand held image display unit or any convention image display platform generally grouped as part of a CT or MRI system.

All data gathered from multiple scans of the patient is to be considered one data set. Each data set can be broken up into smaller units, either pixels or voxels. When the data set is two-dimensional, the image is made up of units called pixels. A pixel is a point in two-dimensional space that can be referenced using two dimensional coordinates, usually x and y. Each pixel in an image is surrounded by eight other pixels, the nine pixels forming a three-by-three square. These eight other pixels, which surround the center pixel, are considered the eight-connected neighbors of the center pixel. When the data set is three-dimensional, the image is displayed in units called voxels. A voxel is a point in three-dimensional space that can be referenced using three-dimensional coordinates, usually x, y and z. Each voxel is surrounded by twenty-six other voxels. These twenty-six voxels can be considered the twenty-six connected neighbors of the original voxel.

In an embodiment of the present invention, a computer-aided system for use in the diagnosis and detection of disease comprises an image acquisition device for acquiring a plurality of image data sets and a processor adapted to classify selected tissue types within the image data sets based on a hierarchy of signal and anatomical models. The processor is further adapted to differentiate anatomical context of the classified tissue types for use in the diagnosis and detection of a selected disease. The system further comprises an interface unit for presenting the classified tissue types within the image data sets and anatomical context of the classified tissue types for aiding an interpretation of the processed image data sets. The anatomical models are parametric, mathematical representations of anatomical tissues. The anatomical context comprises at least one of lung nodules indicative of lung cancer, healthy lung tissue, diseased lung tissue indicative of chronic obstructive pulmonary disease (COPD) and other pathological descriptions of tissue that can be characterized by radiologists and further modeled mathematically. Further discussion of anatomical context and mathematical modeling will be provided with reference to FIG. 4.

In an exemplary embodiment, the imaging device is a x-ray CT scanner. A CT system is particularly well adapted to acquire a plurality of images, or alternatively slices, of a region of interest. Also, in this exemplary embodiment, the imaging object is a lung. It is to be appreciated that other imaging devices that provide a plurality of images, such as magnetic resonance (MR), would also benefit from embodiments of the present invention. Also, it is to be appreciated that other regions of interest other than the lung may be the imaging object, e.g. the heart, colon, limbs, breast or brain. The processing functions performed by processor 120 would be adapted to classify tissue types of interest in these other imaging objects.

An embodiment for a method for detecting disease from the plurality of medical images comprises the steps of acquiring the image data, processing of the acquired image data to define the lung region; computing low level features in the image using the known characteristics of the imaging device and the imaging process; grouping regions in the image, based on their features and an information object hierarchy describing their features, into anatomical structures; and, deciding if any of the grouped regions represents an area which is suspicious for a lung disease. The method further comprises presenting the areas identified as suspicious for lung disease. The presenting step comprises presenting the anatomical context (e.g. lung nodule, diseased tissue, healthy tissue) and a decision process by which the suspicious areas were identified. The grouping of regions is performed using comparisons of signal and anatomical models using Bayes Factors. In a further embodiment, a method for characterizing tissue in medical images for use in disease diagnosis and detection comprises computing an information object hierarchy of increasing complexity to characterize anatomical tissue. The object hierarchy contains models, or alternatively mathematical representations, based on characteristics of an image acquisition device used in acquiring the images and based on anatomical characteristics of a selected region of interest and a specified disease. The grouping, the object hierarchy and Bayes Factor comparisons will be described in greater detail in paragraphs that follow and with reference to FIG. 4.

Figure 2:
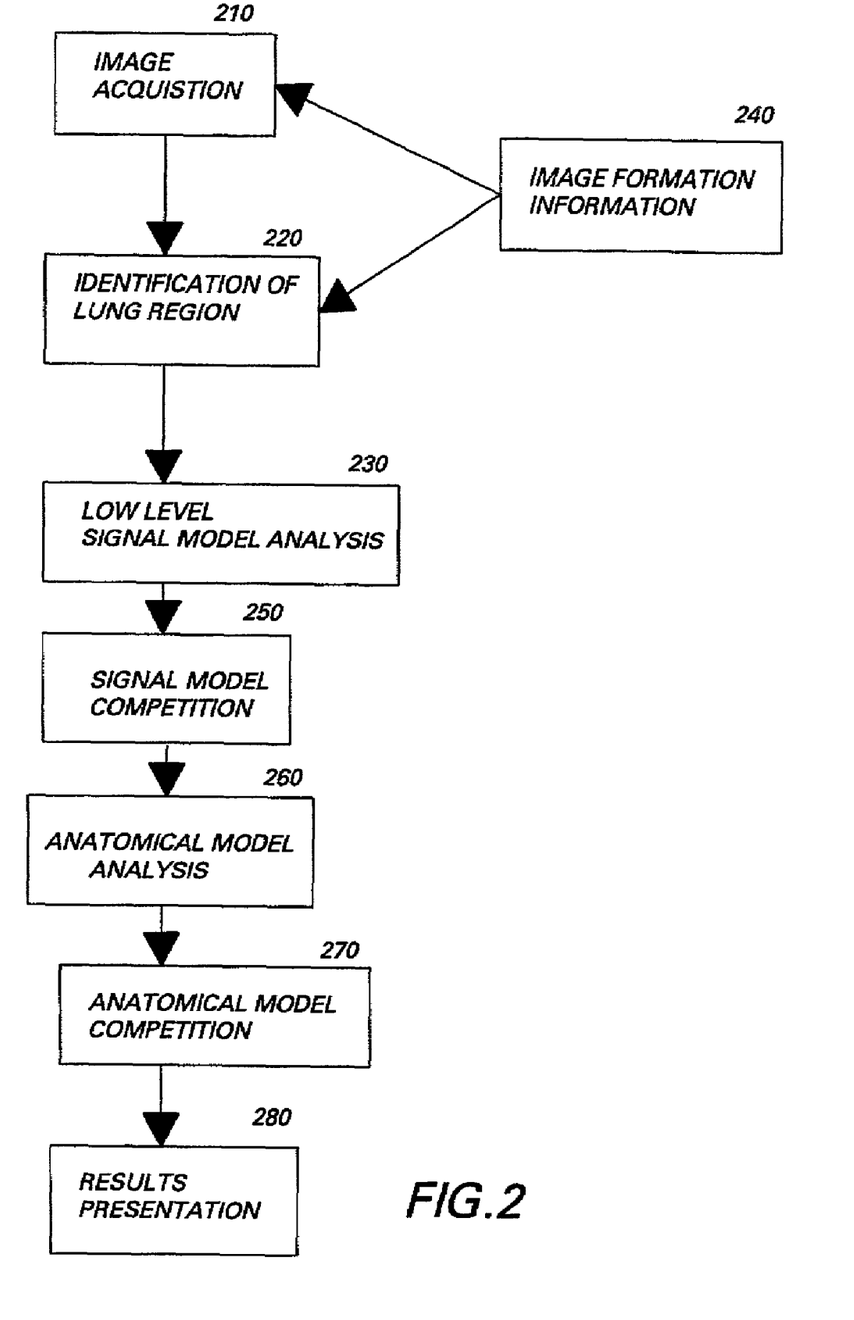
FIG. 2 is a flow diagram of a method for processing image data for use in detecting disease in accordance with embodiments of the present invention.

Referring to FIG. 2, there is shown a more detailed flow diagram of an embodiment of a method for processing image data to be used in detecting disease. Image data is acquired at 210. These images are passed to processor 120 (FIG. 1) for processing steps 220 280 of FIG. 2. At step 220, the area of the images that represents the lung is determined by selection of various known segmentation techniques or, alternatively by an exemplary embodiment of pleural space segmentation which will be discussed in greater detail below with reference to FIG. 3. Resulting from step 220, input pixels from a CT scan are first classified to be either in the lung cavity or outside the lung. The input pixels are acquired from either a two-dimensional CT scan data set or, alternatively, from a three-dimensional CT scan data set. At 230, processor 120 then computes low-level signal models from the gray scale values of the image within the lung region. These models, for example, may include (but are not limited to) compact, bright objects; compact, dark objects; and long, bright objects. The low-level signal models are mathematical descriptions of structures being imaged after the measurement process of the scanner modifies them. Signal model processing continues at 250 to gain more information regarding a region of pixels in the image. In an embodiment of signal model processing for step 250, different signal models are competed against each other in order to best explain a region of pixels in the images. The competition is desirably carried out by performing comparisons between the signal models using the known statistical-based process of Bayes Factors. It is to be appreciated that other decision or statistical based methods may also be used. An exemplary embodiment using Bayes Factors will be described in greater detail below and with reference to FIG. 4.

After decisions have been made regarding the best low-level signal model, a further grouping process occurs at steps 260 and 270. This involves grouping the low-level models into anatomical structures such as particular areas of the lung. Again, the decision process involves competing anatomical models desirably using Bayes Factors in order to make an optimal decision as to model applicability.

Finally, at step 280, results are presented. Results are based on the information provided by the low-level signal models and the anatomical models in order to provide qualitative and quantitative information regarding suspicion for lung disease. Decisions at this level are made in the same way that a radiologist might make decisions regarding a lung nodule because the system has both low-level signal knowledge and anatomical context.

Figure 3:
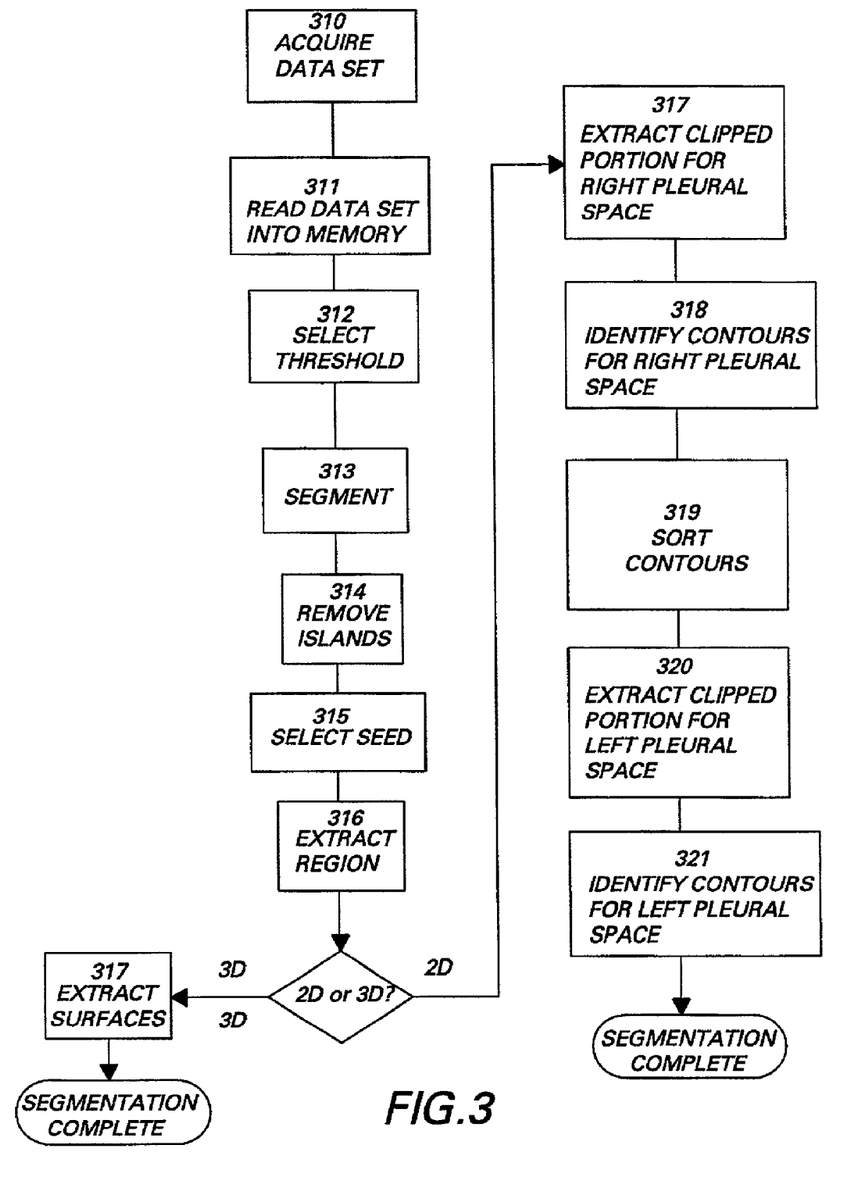
FIG. 3 is a flow diagram of a segmentation method useful in the medical imaging system of FIG. 1; and, FIG. 4 is a block diagram illustration of a modeling method for use in detecting disease in accordance with embodiments of the present invention.

Referring to FIG. 3, an embodiment for identifying the lung region at step 220 is provided. In this embodiment, a lung segmentation process is provided that automatically identifies the boundaries of the pleural space in a Computed Tomography (CT) data set. The boundary is either a set of two-dimensional (2D) contours in a slice plane or a three-dimensional (3D) triangular surface that covers the entire volume of the pleural space. The extracted boundary can be subsequently used to restrict Computer Aided Detection (CAD) techniques to the pleural space. This will reduce the number of false positives that occur when a lung nodule detection technique is used outside the pleural space.

Referring further to FIG. 3, the 3D surface identification proceeds as follows:

310 Acquire a CT data set that covers the lung. The extent of the CT exam should cover the entire region of the pleural space. The centerline landmark of the exam should run approximately down the center of the thorax.

311 Read the CT data set into memory. For efficiency, the data set should reside in contiguous memory, although others means of memory organization are possible.

312 Select a threshold. Select an intensity value that corresponds approximately to air in the CT study. This intensity is called the threshold. The threshold can be chosen using a variety of means, but only needs to be done once per CT lung protocol. The same threshold can be used for all exams using the same protocol (e.g. scanning procedure).

313 Segment the study into foreground and background regions. Replace all samples that have values below the threshold with a positive constant foreground value. Replace all other samples with a 0, the background value. The actual foreground value is arbitrary. Samples marked with the foreground value will correspond to air while samples with a background value will correspond to other tissue.

314 Remove islands in the xy, xz and yz planes. Islands are groups of samples that contain 0 but are surrounded by non-zero samples. Islands are removed by setting their values to the foreground value. Only islands that are below a specified island size are removed. The island size is chosen to be larger than the area of the cross-section of a vessel or bronchial passage and smaller than the area of background outside the CT circle of reconstruction.

315 Select a seed in the pleural space. The seed is located in the middle slice, one quarter of the distance from the left of the image and one half of the distance from the bottom of the image.

316 Extract a 3D connected region. Using the seed as a starting point, mark all values that are connected to the seed, that have the same value as the seed. Other selected connectivity algorithms are also suitable. An exemplary technique is disclosed in U.S. Pat. No. 4,751,643—METHOD AND APPARATUS FOR DETERMINING CONNECTED SUBSTRUCTURES WITHIN A BODY.

317 Extract surfaces. Extract a surface comprised of triangles using an isosurface extraction technique. The isosurface corresponds to a value midway between the foreground and background values. Any isosurface extraction technique can be used. An exemplary isosurface extraction technique is the well-known Marching Cubes algorithm as described in U.S. Pat. No. 4,710,876—SYSTEM AND METHOD FOR THE DISPLAY OF SURFACE STRUCTURES CONTAINED WITHIN THE INTERIOR REGION OF A SOLID BODY.

The 2D contour identification proceeds as follows. Steps 310–316 correspond to steps 310–316 for the 3D surface.

310 Acquire a CT data set that cover the lungs.

311 Read the CT data set into memory.

312 Select a threshold.

313 Segment the study into foreground and background regions.

314 Remove islands in the xy, xz and yz planes.

315 Select a seed for the pleural space.

316 Extract a 3D connected region.

317 Extract a clipped portion of the volume data set that corresponds to the right pleural space. The clipped region should extent beyond the centerline of the data by a fixed percentage. This is to accommodate plural cavities that may cross the centerline. A 20% overlap seems appropriate for lung studies.

318 Identify the contours in the left plural space. Extract contours comprised of line segments using a contour extraction technique. Any contour extraction technique can be used. An exemplary embodiment is the Marching Squares algorithm, a specialization of Marching Cubes described in U.S. Pat. No. 4,710,876—SYSTEM AND METHOD FOR THE DISPLAY OF SURFACE STRUCTURES.

319 Sort the contours by line segment count and keep the contour with the largest number of line segments. This contour corresponds to the right pleural space.

320 Extract a clipped portion of the volume data set that corresponds to the left pleural space. This is the same as step 318 except the clipping region is specified from the right side of the images.

321 Identify the contours of the left plural space. This is the same as step 318, applied to the region in step 320. This contour corresponds to the left pleural space.

Employing the above described embodiments of the segmentation process, enables an automatic selection of all algorithm parameters based on the specific anatomy of the lung and the CT examination protocol. Further, the island removal is performed in three consecutive second passes, each in a different plane. It is to be appreciated that identifying the lung region initially allows a reduction in computation time and complexity for the downstream measurements.

Figure 4:
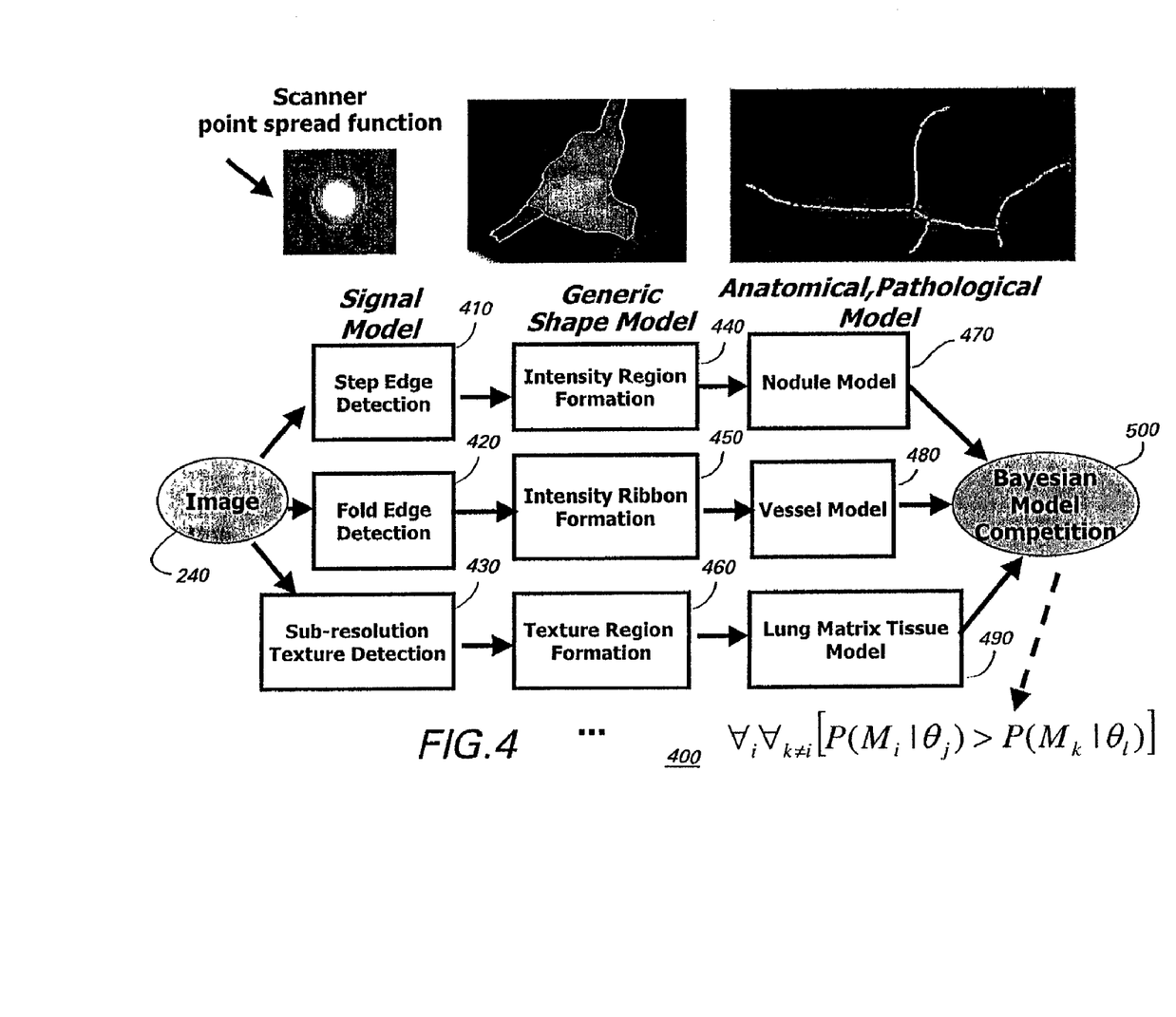

Referring to FIG. 4, an embodiment of a hierarchy of models to be used in the method of FIG. 2 and a method for processing within the hierarchy are provided. The hierarchy of models comprise models of various levels comprising signal model data, geometric model data, and anatomical model data. Those pixels that have been classified as being inside the lung region at step 220 (FIG. 1) are modeled at several levels of modeling structure, herein after referred to as the hierarchy. As used herein, models refer generally to mathematical representations or, alternatively, mathematical translations.

At a first or low level, characteristics of the imaging device are translated into mathematical representations. Characteristics of the imaging device that are of interest are those characteristics that generally affect the display and resolution of the images or otherwise affect a radiologist's interpretation of regions in the image. For example, the scanner point spread function is a measurable indicator of the image formation process and may be mathematically modeled. Other indicators of the image formation process include X-ray density, brightness, resolution and contrast.

At a second or intermediate level, fitted shape models are derived to explain the geometry and intensity surface of various tissues. Shape and geometric model information is derived from anatomical information and expert radiologist observations which will be described in greater detail with respect to FIG. 4.

With one pass through the hierarchy, low-level pixel information (X-ray density) is transformed into anatomical information. This anatomical information is a classification of all pixels into lung tissue types, e.g. blood vessel, lung matrix, and lung cancer nodule. The models for the intermediate level are generally derived from pathological information for a region of interest (e.g. lung) and a specific disease (e.g. lung cancer or COPD) obtained from expert information, for example radiologists that have observed recurring characteristics for certain types of lung disease. The expert information is desirably from a radiologist or a plurality of radiologists experienced with the region of interest and detection of the specific disease.

The models described above create a hierarchy of information objects of increasing radiological importance that are explicitly modeled. For example, as is shown in FIG. 4, lung nodules and vascular structure are indicators of lung disease such as lung cancer. Additionally, lung parenchyma metrics are also indicators of lung disease. Based on radiologists observations, or alternatively, other disease experts, a set of geometric and shape characteristics are obtained. For example, lung cancer nodules are generally compact, bright and spherical in nature. Further, lung cancer nodules that are likely to be cancerous tend to be spiculated (spidery vessel structures). In embodiments of the present invention, these characterizations of disease, such as lung cancer nodules, are mathematically represented as nodule model 470 and vessel model 480 as shown in FIG. 4. Of further interest is lung matrix tissue which can be considered background to the vessels and nodules and for embodiments of the present invention is also modeled as the mathematical representation of lung matrix tissue model 490.

Referring further to FIG. 4, nodule model 470, vessel model 480 and lung matrix tissue model 490 represent a high level explanation in the hierarchy used to distinguish various lung tissues. Each of the high level models are further defined at low and intermediate levels. For example, nodules are generally spherical and bright (measurable in Hounsfeld units). Thus, a shape model representing intensity region formation 440 and a signal model for step edge detection 410 are derived mathematically to enable identification of a potential nodule. In a further example, spiculated nodules tend to have a compact core structure fed by one or more vessels and also having a spidery or spiculated structure. A shape model representing intensity ribbon formation 450 and a signal model representing fold edge detection 420 similarly enable identification of a potential spiculated nodule. Background lung tissue is also similarly defined by low and intermediate levels of a texture region formation model 460 and a sub-resolution texture detection model 430.

At each level of the hierarchy, decisions are made via estimation of model parameters as to the characteristics of each information object, that is, each increasingly high-level explanation of the pixels in the images. The modeling steps at each level of the hierarchy.

1) Pixel information as the output of an image formation process; and,

2) Fitted shape models are derived to explain the geometry and intensity surface of various tissues.

In the first modeling step (step edge detection 410), pixel information is analyzed at the output of an image formation process (240 of FIGS. 1 and 2). The tissue boundaries are identified using convolution operators. Nodule candidates are localized by convolving the images with differential kernels defined by the signal impulse response of the imaging device. In an embodiment, images acquired from a GE LightSpeed Scanner were used and a Canny edge detector was used with a smoothing parameter of 1.1 pixels. An embodiment of the Canny edge-detection algorithm can be found in a description of Canny 86.

The vascular structure is localized by convolving the images with differential kernels defined by the signal impulse response of the imaging device using fold edge detection 420. In this embodiment using images acquired from a GE LightSpeed Scanner, a fold edge detector was used with a smoothing parameter of 1.5 pixels.

Background tissue is represented as sub-resolution texture by sub-resolution texture detection 430. Background tissue is localized by identifying regions of low intensity. Convolution kernels defined by the signal impulse response of the imaging device are used to identify potential background regions. In this embodiment using images acquired from a GE LightSpeed Scanner, a Canny edge detector is used with a smoothing parameter of 1.1 pixels. At this stage of processing, the list of background regions is trimmed by thresholding at an average intensity of 520. An alternate localization procedure consists of modeling the background tissue as generalized intensity cylinders with random orientation. In this implementation, localization is achieved by comparing the output of generalized-cylinder model with the image intensities.

In the second modeling step, fitted shape models are used to explain the geometry and intensity surface of the various tissues. Putative nodule candidates are formed by grouping the output of the signal model stage into regions at intensity region formation step 440. Region grouping is performed by extrapolating edge segments perpendicular to the edge gradient. Edges ending near vertices associated with other edges are connected to form regions. In this implementation, the distance threshold for connecting edge segments is 4 pixels.

The vascular structure is obtained at intensity ribbon formation step 450 by linking together the output of the fold edge detection 420. At each point on the chain, a width of the chain is defined by locating the nearest step-edge on each side in a direction perpendicular to the chain direction. Through this sweeping operation, a set of intensity ribbons is defined. These ribbons are implicitly defined by the centerline of the fold-edges and the width of the fold along its entire length. These ribbons are considered "candidate vessels", that is, objects which may be defined as blood vessels in the next level of the hierarchy.

At step 460 (Texture region formation), background lung tissue and lung matrix tissue are modeled. Background lung tissue is obtained by grouping together regions output by the signal operators. Regions are formed by extrapolating edge segments perpendicular to the edge gradient. Edges ending near vertices associated with other edges are connected to form regions. In this implementation, the distance threshold for connecting edge segments is 4 pixels.

Turning now to the decision process to determine which of the candidate nodules found in modeling step 2 are true lung cancer nodules. At this point, there are essentially two competing segmentations of the CT image—a region segmentation and a ribbon segmentation. Each region is a candidate nodule, and it must be decided whether the region, with an appropriate model on pixel intensities and region shape, is a better explanation of its interior pixels than any possible vessel or background explanation. To accomplish this, the two models are compared at step 500 using the Bayes Factor. The competition framework is a pair wise comparison of the modeled information: nodule vs. vessel, and nodule vs. background. If the nodule "wins" each competition, then it is considered a suspicious region and is reported as such.

As used herein, "Bayes Factors" refer to a known decision mechanism to ensure that the optimal decision is made given the input parameters. Applying the Bayes Factor to embodiments of the present invention provides that optimal decisions will be made given the statistical models of the shapes and signals provided by the radiologists' expert observations. This optimality assumes the statistical models of each anatomy type represent all the relevant knowledge embodied in a trained radiologist, and that the radiologist acts in a rational manner as defined by the Bayes Factor mechanism. Thus, the hierarchy of information enables processing to make a same decision as a radiologist would make regarding a region or nodule. Also, as used herein Bayes Factors will be used interchangeably herein with the term "Bayesian model competition".

To begin the competition, for each candidate nodule a patch of pixels around the candidate is considered. In the nodule vs. vessel competition, this patch is defined as the union of the candidate nodule and each conflicting ribbon, in turn. In the nodule vs. background competition, the patch is defined as all pixels below a pre-specified intensity threshold within a pre-specified radius of the geometric center of the candidate, unioned with the candidate nodule. The radius is desirably set to 10 pixels, and the intensity threshold is desirably set to 520 CT units. Once the competition patch has been defined, each of the two competitions proceed in the same fashion. The following table gives all the information that is available during processing.

TABLE 1

| Notation | Description |
| --- | --- |
| x | intensity data |
| $\theta_1$ | geometrical measurement on "model 1", eg. "one nodule, background elsewhere" |
| $\theta_2$ | geometrical measurement on model 2, eg. "one ribbon, background elsewhere" |
| $p(x|M = 1, \beta_1, \theta_1)$ | intensity model given that Model 1 is correct ($\beta$ is a nuisance parameter) |
| $p(x|M = 2, \beta_2, \theta_2)$ | intensity model given that Model 2 is correct |
| $p(\beta_1|M = 1)$ | prior distribution on the intensity model nuisance parameter, given model 1 is correct |
| $p(\beta_2|M = 2)$ | prior distribution on the intensity model nuisance parameter, given model 2 is correct |
| $p(\theta_1|M = 1)$ | prior distribution on the geometrical parameters in model 1 |
| $p(\theta_2|M = 2)$ | prior distribution on the geometrical parameters in model 2 |
| $p(M = 1)$ | prior probabilities on model 1 (the "incidence" of model 1) |
| $p(M = 2)$ | prior probabilities on model 2 |

In each row of Table 1, the notation p(a|b) indicates the conditional probability distribution on the random variable a given the value of the random variable b.

The intensity model $x_i$, given the candidate nodule is correct as a normal distribution with mean equal to a 2 parameter parabaloid, and constant variance, is defined as:

$$x_i = \beta_0 + \beta_1 u_i^{*2} + \beta_2 v_i^{*2} + \epsilon_i \quad (1)$$

where $(u_i, v_i)$ is the two-dimensional location of the ith pixel, after a rotation and translation that forces the least squares estimates of all other parameters in the full 6-parameter parabaloid in two dimensions to be zero. The error term $\epsilon_1$ is normally distributed with zero mean and fixed variance, estimated off-line from true nodule data. As used herein, "off-line" estimation refers to known information learned or known beforehand, such as chances or likelihood information.

The intensity model given the vessel is correct as a two-parameter parabaloid is defined as:

$$x_i = \beta_0 + \beta_1 u_i^{*2} + \epsilon_i \quad (2)$$

where in this case $u_i$ is defined as a unit vector in the direction normal to the fold-edge chain direction. The fold edge center of the ribbon is defined as $u_i=0$. Spans are defined at one-pixel separation along the chain, and each span's intensity data is modeled independently according to the above model. The error term is again normally distributed.

The background model is defined as independent normal data at each pixel with unknown mean and fixed variance, estimated off-line from true background data. This data is gathered by an expert and the variance is estimated using the usual normal-model unbiased estimate.

Prior distributions are defined on all intensity model parameters as normal distributions with means and covariance matrices estimated off-line from manually segmented intensity data. Prior distributions on shape parameters are defined as uniform distributions on key shape characteristics like nodule aspect ratio and size. Prior probabilities on each model are determined via a known scanner parameter known as Receiver Operating Characteristic curves according to pre-specified sensitivity and specificity targets.

To decide the winner of each competition, the Bayes Factor is calculated. The Bayes Factor as used herein refers to the ratio of posterior model probabilities given the intensity and shape data calculated in the last level (Step 3) of modeling hierarchy for two given models M=1 and M=2, $$\frac{p(M = 1 | x, \theta_1, \theta_2)}{p(M = 2 | x, \theta_1, \theta_2)}. \quad (3)$$

This ratio can be written as $$\frac{p(M = 1 | x, \theta_1, \theta_2)}{p(M = 2 | x, \theta_1, \theta_2)} = \frac{\begin{array}{c}p(x | \theta_1, M = 1)p(\theta_1 | M = 1) \\ p(\theta_2 | \theta_1, M = 1)p(M = 1)\end{array}}{\begin{array}{c}p(x | \theta_2, M = 2)p(\theta_2 | M = 2) \\ p(\theta_1 | \theta_2, M = 2)p(M = 2)\end{array}} \quad (4)$$

where the factor $$\frac{p(\theta_2 | \theta_1, M = 1)}{p(\theta_1 | \theta_2, M = 2)} \quad (5)$$

is assumed equal to one. The Bayes factor is necessarily greater than zero, and it indicates evidence for model 1 if the factor is greater than one (and vice versa).

Candidate nodules which give Bayes factors greater than one in both competitions are deemed suspicious, and are superimposed the CT data in a visualization tool (presenting step 280 of FIG. 2). The characteristics of these suspicious nodules are also stored for further follow-up.

It is to be appreciated that incorporating knowledge about the imaging processing and the imaging device into the analysis techniques increases the accuracy and robustness of image measurements. The competition framework provides a robust method for making a model selection decision. Modeling the anatomy in the images improves the robustness of the image measurements and allows results to be presented to doctors in the context of the anatomy. The anatomical models are easily explained to physicians and their expert knowledge is coherently incorporated into the system (in the form of mathematical approximations of anatomical features). The lowest level of the modeling hierarchy relies on time-tested image formation and understanding techniques which are firmly grounded in human visual perception. Anatomical models are chosen via Bayes Factors, enable optimal decision given our statistical models. No training data (such as the voluminous training data needed for neural networks) is required, but it can be used to supplement expert knowledge in the specification of prior distributions. The model-based approach allows incorporation of expert information elicited from radiologists. The results are reported to a radiologist or doctor incorporating the anatomical context of each suspicious region and the decision process by which suspicious regions were identified.

In a further embodiment, the results are reported to a radiologist or doctor (hereinafter "user") in a manner that the user receives anatomical context, reasons for the decision of whether the region is of a particular type (nodule or vessel), and information of importance to the user. Information of radiological importance are, for example, size of nodule, number of vessels, evidence of spiculation, chances/likelihood of cancer or disease, brightness measurements and other characteristic information related to the disease at issue. Processor 120 of FIG. 1 is adapted to perform the computations needed to support this reporting functionality. In a further embodiment, processor 120 is adapted to allow for user queries regarding particular regions of interest such as pointing to a region and receiving information such as size, number of vessels and brightness for the selected region.

The embodiments above related to lung cancer detection and specifically to the distinction between lung nodules and vessels. In further embodiments, additional lung disease characteristics are similarly modeled such as the low-density, sponge-like texture which is generally characteristic of emphysema. As was described with reference to nodules and vessels, anatomical feature descriptions are obtained by experts (e.g. radiologists) and mathematically represented as a hierarchy. In further embodiments, models are derived for diseases that occur in other areas, such as the brain, colon and heart.

Also, in a further embodiment, the hierarchy of models may be used in known neural network techniques as the training data to identify low and intermediate information and prior distributions. It is desirable that the Bayes Factor analysis be applied at the higher levels to provide useful and interpretative diagnosis data and the decision process.

In a further embodiment, processor 120 is further adapted to store the anatomical context and processed image data sets to be searched and retrieved remotely. In this embodiment, the information developed at each level in the model hierarchy is stored in systems used for medical archives, medical search and retrieval systems and alternate medical disease reporting systems. Further in this embodiment, information that may be searched and retrieved include: pathological and anatomical models derived for characteristics of diseases, images representative of the diseases, and results of the model hierarchy computations (processed image data sets). The capability of storing/retrieving information for a particular diseased tissue type enables broader access to the information, such as via the Internet, a hospital information system, a radiological information system, or other information transmission infrastructure. Additionally, this information allows matching and retrieval of exams classified as similar based on the information provided by model hierarchy computations.

In further embodiments, processor 120 is adapted to automatically send detailed exam information to remote workstations or portable computing device via an information transmission infrastructure. In a further embodiment of processor 120, processor 120 is adapted to automatically send detailed exam information which meets selected specified requirements determined in advance of transmission or determined adaptively by the processing system. In order to further tune or adjust analysis programs, processor 120 is also adapted to tune at least one computer analysis algorithm based on information from model hierarchy computations stored in previous exams.

Also, in another further embodiment, processor 120 is further adapted to generate statistical measurements based on the information from model hierarchy computations stored in previous exams and report results of the statistical measurements to a local or remote monitoring facility. In this embodiment, processor 120 may also be configured to report the results of the statistical measurements if predetermined criteria based on the system performance are met.

In an exemplary embodiment, the steps outlined in the last section are implemented in C++ code based on the Targetjr image understanding library (http://www.targetjr.org). A set of DICOM (Digital Image and Communication in Medicine) image files, one for each slice in the CT scan, are input into the program and the program returns suspicious nodules to be visualized on the original CT data or saved for further follow-up. It is to be appreciated that other coding software known to one skilled in the art would not depart from the spirit of the invention.

The embodiments of the invention presented in previous paragraphs focus on the problem of locating suspicious regions in CT lung scans. It is to be appreciated that the hierarchical image modeling framework can be directly transferred to other imaging modalities (for example MRI, X-ray, ultrasound scanner, positron emission tomography (PET) scanner) and diseases by re-specifying the low-level detection techniques and the statistical distributions of anatomy.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

The invention claimed is:

1. A method for characterizing tissue in medical images for use in disease diagnosis and detection comprising:
computing an information object hierarchy of increasing complexity to characterize anatomical tissue, the object hierarchy containing models based on oharacleristios an image acquisition device and anatomical characteristics of at least one given disease, wherein the hierarchy comprises a low level corresponding to signal models reoresentative of the image acquisition device and a high level corresponding to anatomical models derived in accordance with expert observation and knowledoe of the at least one given disease;
comparing information by performing Bayesian competition using Bayes Factors at respective levels of the object hierarchy to identify suspicious tissue indicative of disease, wherein the Bayes Factor is a ratio of posterior model probabilities given intensity and share data for two given models M=1 and M=2, and where x=intensity data, $\theta_1$=geometric model for M=1 and $\theta_2$=geometric model for M=2 and is expressed as:

$$\frac{p(M=1 \mid x, \theta_1, \theta_2)}{p(M=2 \mid x, \theta_1, \theta_2)}.$$

2. The method of claim 1 wherein the anatomical characteristics are at least one of geometric shape and intensity values.

3. The method of claim 1 wherein the object hierarchy further comprises a plurality of signal models based on characteristics of an image acquisition device used in acquiring the images and plurality of models based on anatomical characteristics of a selected region of interest and the at least one given disease.

4. The method of claim 1 further comprising a plurality of intermediate levels defining geometric models, shape models, intensity models derived from the anatomical models at the high level.

5. The method of claim 1 where the at least one given disease is lung disease.

6. The method of claim 1 wherein the anatomical models at the high level correspond to lung nodules indicative of lung disease, vascular structure and lung matrix tissue.

7. The method of claim 6 further comprising a plurality of intermediate levels defining shape models and intensity models characteristic of lung nodules.

8. The method of claim 6 further comprising a plurality of intermediate levels defining shape models and intensity models characteristic of lung vascular structure.

9. A system for processing medical images acquired by an image acquisition device for use in the detection and diagnosis of disease comprising:
- a processor coupled to the image acquisition device, the processor is adapted to identify suspicious regions within the medical images based on an information object hierarchy and a Bayes Factors competition framework using at least one of anatomical models and signal models; and,
- an interface coupled to the processor adapted to present information relating to the suspicious regions identified by the processor, the information being used for diagnosis and detection;
- wherein the Bayes Factor competition uses the Saves Factor, the Saves Factor being to a ratio posterior model probabilities given intensity and shape data for two given models M=1 and M=2, and where x=intensity data, $\theta_1$=geometric model for M=1 and $\theta_2$=geometric model for M=2 and is expressed as:

$$\frac{p(M=1\mid x, \theta_1, \theta_2)}{p(M=2\mid x, \theta_1, \theta_2)}.$$

10. The system of claim 9 wherein the anatomical models comprise at least one of lung nodules and vascular structure indicative of lung disease.

11. The system of claim 9 wherein the hierarchy comprises models of increasing complexity for use in identifying suspicious regions.

12. The system of claim 9 wherein the interface is further adapted to receive user queries regarding an anatomical context of the suspicious regions and a decision process for identifying each of the suspicious regions.

13. The system of claim 9 wherein the signal models comprises at least one of a scanner point spread function, the impulse response of the image acquisition device arid the X-ray density, brightness, resolution and contrast of anatomical structures.

14. The system of claim 9 wherein the image acquisition device is selected from at least one of a computed tomography (CT) scanner, a magnetic resonance imaging (MRI) scanner, an ultrasound scanner, and a positron emission tomography scanner, and a X-ray device.

15. The system of claim 9 wherein the processor is further adapted to automatically segment the pleural space.

16. The system of claim 9 wherein the processor is further adapted to group a plurality of anatomical and signal models into the hierarchy of models for use in the competition framework.

17. The system of claim 9 wherein the medical images are acquired of at least one of a lung, a colon, a breast, a brain and a limb.

* * * * *